(12) United States Patent
Schwanz

(10) Patent No.: US 7,934,846 B1
(45) Date of Patent: May 3, 2011

(54) WELDING HELMET HAVING AN AUTOMATIC LIGHTING SYSTEM

(76) Inventor: Kenneth H. Schwanz, Portage, WI (US)

( * ) Notice: Subject to any disclaimer, the term of this patent is extended or adjusted under 35 U.S.C. 154(b) by 66 days.

(21) Appl. No.: 12/460,872

(22) Filed: Jul. 24, 2009

(51) Int. Cl.
*F21V 21/084* (2006.01)
(52) U.S. Cl. .......................................... 362/106; 362/103
(58) Field of Classification Search .................. 362/103, 362/105, 106
See application file for complete search history.

(56) References Cited

U.S. PATENT DOCUMENTS

| 3,227,866 A * | 1/1966 | Peters et al. .................. 362/105 |
| 4,332,004 A | 5/1982 | Slaughter |
| 4,958,264 A | 9/1990 | Evendon |
| 5,191,468 A | 3/1993 | Mases |
| 6,340,234 B1 * | 1/2002 | Brown, Jr. ..................... 362/105 |
| 7,161,116 B2 | 1/2007 | Steinemann |
| 7,178,932 B1 | 2/2007 | Buckman |

* cited by examiner

*Primary Examiner* — David V Bruce
(74) *Attorney, Agent, or Firm* — Richard L. Miller

(57) ABSTRACT

A welding helmet having a headband that fits upon a head of a welder, and a face shield with a viewing port having a light filtering window that pivots on the headband between a raised up non-shielding position and a lower down shielding position has an automatic lighting system with a power source component secured to a interior bottom surface of a top portion of the face shield, and an illumination component secured to a top exterior surface of the top portion of the face shield for lighting a work area outside the helmet. The energizing of the lighting system is responsive to the position of the raising and lowering of the face shield of the helmet so as to permit the welder to better perceive his/her surroundings.

22 Claims, 4 Drawing Sheets

WELDING HELMET HAVING AN AUTOMATIC LIGHTING SYSTEM

BACKGROUND OF THE INVENTION

1. Field of the Invention

The present invention relates to a welding helmet, and more particularly, a welding helmet having an automatic lighting system.

2. Description of the Prior Art

Numerous innovations for helmets having lighting devices have been provided in the prior art that will be described. Even though these innovations may be suitable for the specific individual purposes to which they address, however, they differ from the present invention.

A FIRST EXAMPLE, U.S. Pat. Office Document No. 4,332,004, Issued on May 25, 1982, to Slaughter teaches a lighting system for a welders helmet which includes a high intensity, high Kelvin temperature electric light source attached to the face shield for directing a high energy, high Kelvin temperature light beam forwardly of the viewing port, and an energizing circuit including an on-off switch interconnecting the light source to a source of electrical energy which de-energizes the light source where the welder's eyes are not protected by the face shield.

A SECOND EXAMPLE, U.S. Pat. Office Document No. 4,958,264, Issued on 09-18-1990, to Evendon teaches a lamp for use with a protective helmet having a visor mounted thereon by means of pivots. The lamp comprises a band adapted to extend around the back of the helmet and securing means, whereby the ends of the band can be releasably secured to the pivots of the visor.

A THIRD EXAMPLE, U.S. Pat. Office Document No. 5,191,468, Issued on Mar. 2, 1993, to Mases teaches a welder's helmet provided with a fast filter which is controlled by welding light and through which the wearer of the helmet can see clearly in the absence of welding light. In accordance with the invention, the helmet is complemented with side windows operative to filter out IR and UV radiation and having a moderate filter effect for visible light.

A FOURTH EXAMPLE, U.S. Pat. Office Document No. 6,340,234, Issued on Jan. 22, 2002, to Brown Jr. teaches a means to illuminate the lens of a face shield to be worn by a welder. The lens is illuminated to enable the welder to see through the lens prior to the welding arc being lighted. The face shield is equipped with a size adjustable head band. Multiple lights are disposed around the frame of the lens and an on/off switch is provided along with a time delay button. The lights are powered by a battery which is disposed in the frame. The present invention can be retrofitted onto existing helmets or manufactured as an integral part of new helmets/face shields.

A FIFTH EXAMPLE, U.S. Pat. Office Document No. 7,161,116, Issued on Jan. 9, 2007, to Steinemann teaches a welding protective mask which includes illumination equipment for illuminating a work area. The illumination equipment includes an illumination device, a detection device for detecting an ambient light intensity, an energy storage for electrically supplying the illumination equipment and controller for controlling an intensity of light radiated by the illumination means according to the ambient light intensity. In a preferred embodiment of the invention the controller is set up to detect a welding process with a flicker circuit and to switch off the illumination device during the welding process.

A SIXTH EXAMPLE, U.S. Pat. Office Document No. 7,178,932, Issued on Feb. 20, 2007, to Buckman teaches an apparatus which discloses an improved welders helmet having a replaceable lens thereon incorporating an electrically driven fan which receives filtered air through a plurality of air ducts having a filter thereon. A receptacle for containing a battery is disposed on the helmet along with photovoltaic elements for recharging the batteries from the flash of the weld. Lights are also disposed on the helmet.

It is apparent now that numerous innovations for helmets having lighting devices have been provided in the prior art that adequate for various purposes. Furthermore, even though these innovations may be suitable for the specific individual purposes to which they address, accordingly, they would not be suitable for the purposes of the present invention as heretofore described.

SUMMARY OF THE INVENTION

AN OBJECT of the present invention is to provide a welding helmet having an automatic lighting system that avoids the disadvantages of the prior art.

ANOTHER OBJECT of the present invention is to provide a15 welding helmet having an automatic lighting system that is simple and inexpensive to manufacture.

STILL ANOTHER OBJECT of the present invention is to provide a welding helmet having an automatic lighting system that is simple to use.

BRIEFLY STATED, STILL YET ANOTHER OBJECT of the present invention is to provide a welding helmet having an automatic lighting system which comprises the welding helmet having a headband that fits upon a head of a welder, and a face shield with a viewing port having a light filtering window that pivots on the headband between a raised up non-shielding position and a lower down shielding position. The automatic lighting system has a power source component secured to a bottom surface of a top portion of the face shield, and an illumination component secured to a top surface of the top portion of the face shield. The power source component is electrically connected to the illumination component. When the face shield is pivoted to the raised up non-shielding position the power source component will de-energize the illumination component. When the face shield is pivoted to the lower down shielding position the power source component will energize the illumination component to produce light beam from the illumination component mounted on the exterior of the helmet, so that the welder can see the light area around him/her and be able to navigate and better position himself/herself while the face shield is in a down position.

If the light filtering window in viewing port of the helmet is provider with an auto darkening glass lens the present invention actually permits the welder to see his/her surroundings through such a lens. Alternatively even when the light filtering window in viewing port of the helmet is only provider with a regular standard dark glass lens the present invention still provides some benefit if it is aimed downwardly toward the welders feet by permitting him/her to utilize his peripheral vision to better perceive of his/her surroundings.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawings are briefly described as follows.

Figure 1:
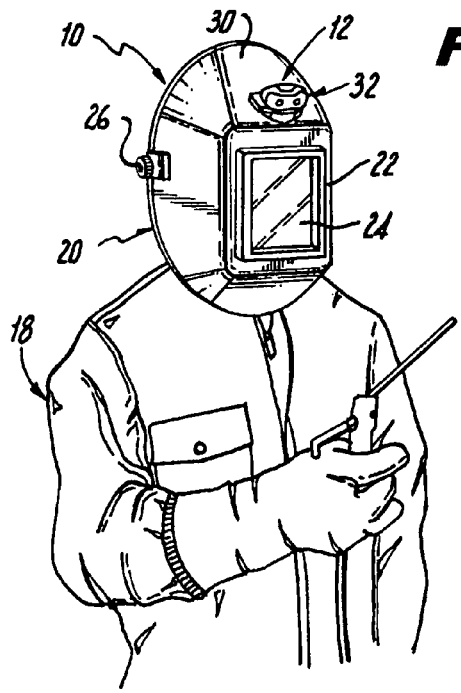
FIG. 1 is a diagrammatic perspective view of an embodiment of the present invention worn by a welder.

A MARSHALING OF REFERENCE NUMERALS UTILIZED IN THE DRAWING 10 welding helmet
12 automatic lighting system
14 headband of welding helmet 10
16 head
18 welder
20 face shield of welding helmet 10
22 viewing port of face shield 20
24 light filtering window in viewing port 22
26 pivot member
28 power source component of automatic lighting system 12
30 top portion of face shield 20
32 illumination component of automatic lighting system 12
34 forward light beam
36 battery of power source component 28
38 gravity sensitive tilt switch of power source component 28
40 on/off power switch of power source component 28
42 female socket of power source component 28
44 case of power source component 28
46 removable cover of case 44
47 with mating hook and loop pile fastener material
48 light emitting diode of illumination component 32
50 multiple position switch of illumination component 32
52 base member of illumination component 32
54 headlamp housing of illumination component 32
56 hinge between base member 52 and headlamp housing 54
58 electrical wire
60 male plug on electrical wire 58

DETAILED DESCRIPTION OF THE PREFERRED EMBODIMENT

Figure 2:
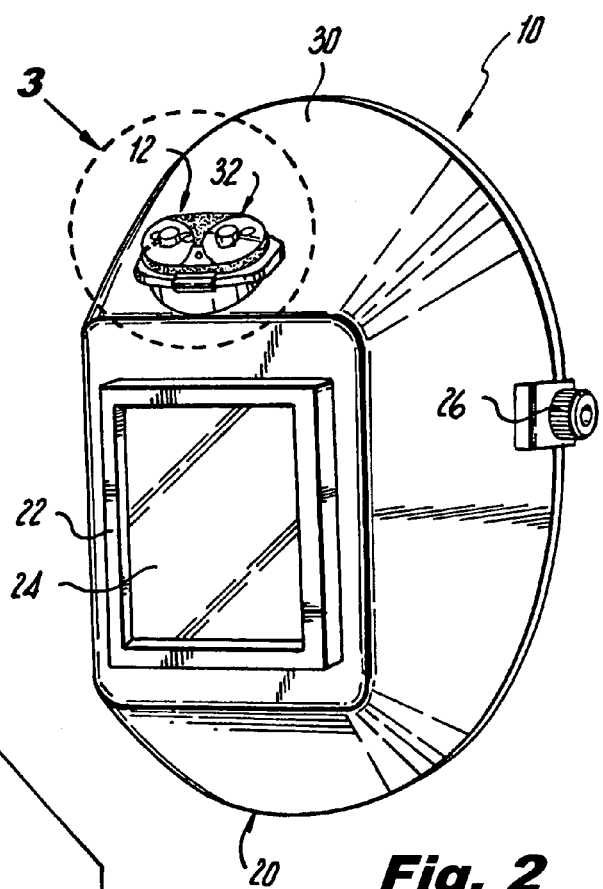
FIG. 2 is an enlarged diagrammatic perspective view of the present invention per se.
Figure 3:
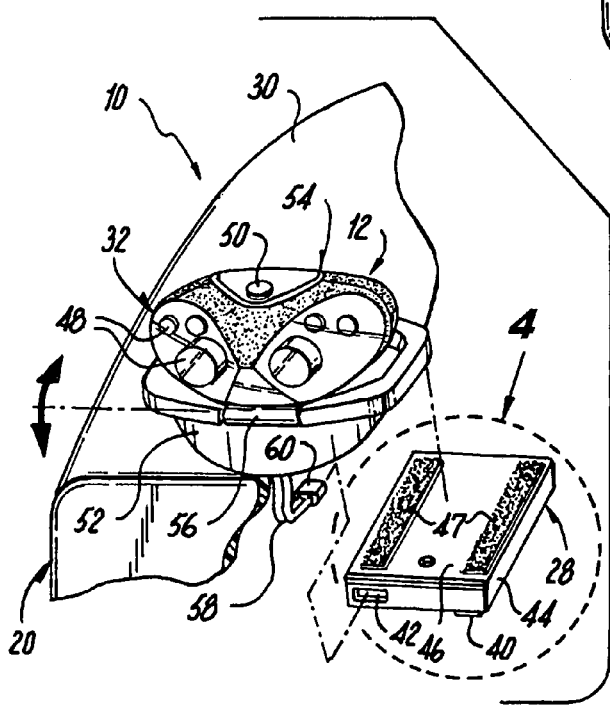
FIG. 3 is a further enlarged perspective view, with parts broken away, showing in greater detail the automatic lighting system taken in the area enclosed in the dotted circle indicated by arrow 3 in FIG. 2.
Figure 4:
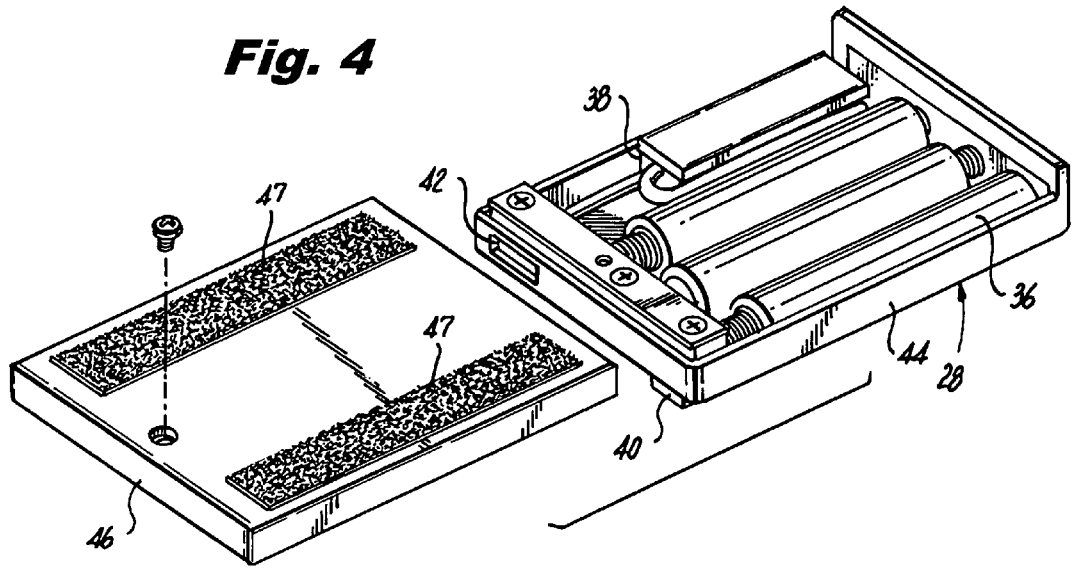
FIG. 4 is a still further enlarged diagrammatic perspective view taken of the area enclosed in the dotted curve indicated by arrow 4 in FIG. 3, with the cover exploded showing the batteries, gravity sensitive tilt switch and associated components therein.
Figure 5:
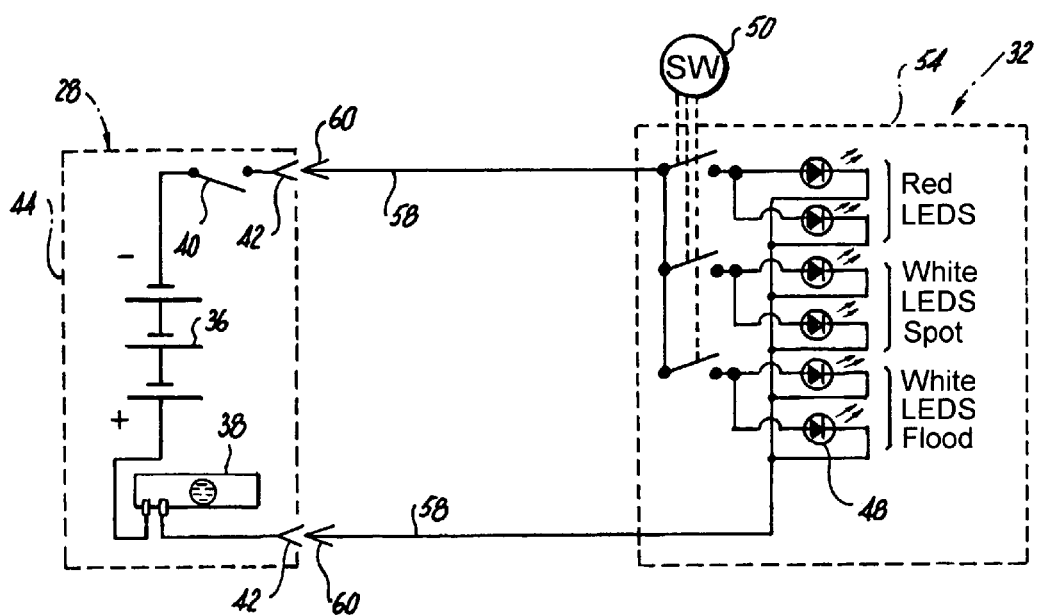
FIG. 5 is a schematic diagram of the electrical circuit of the automatic lighting system.
Figure 6:
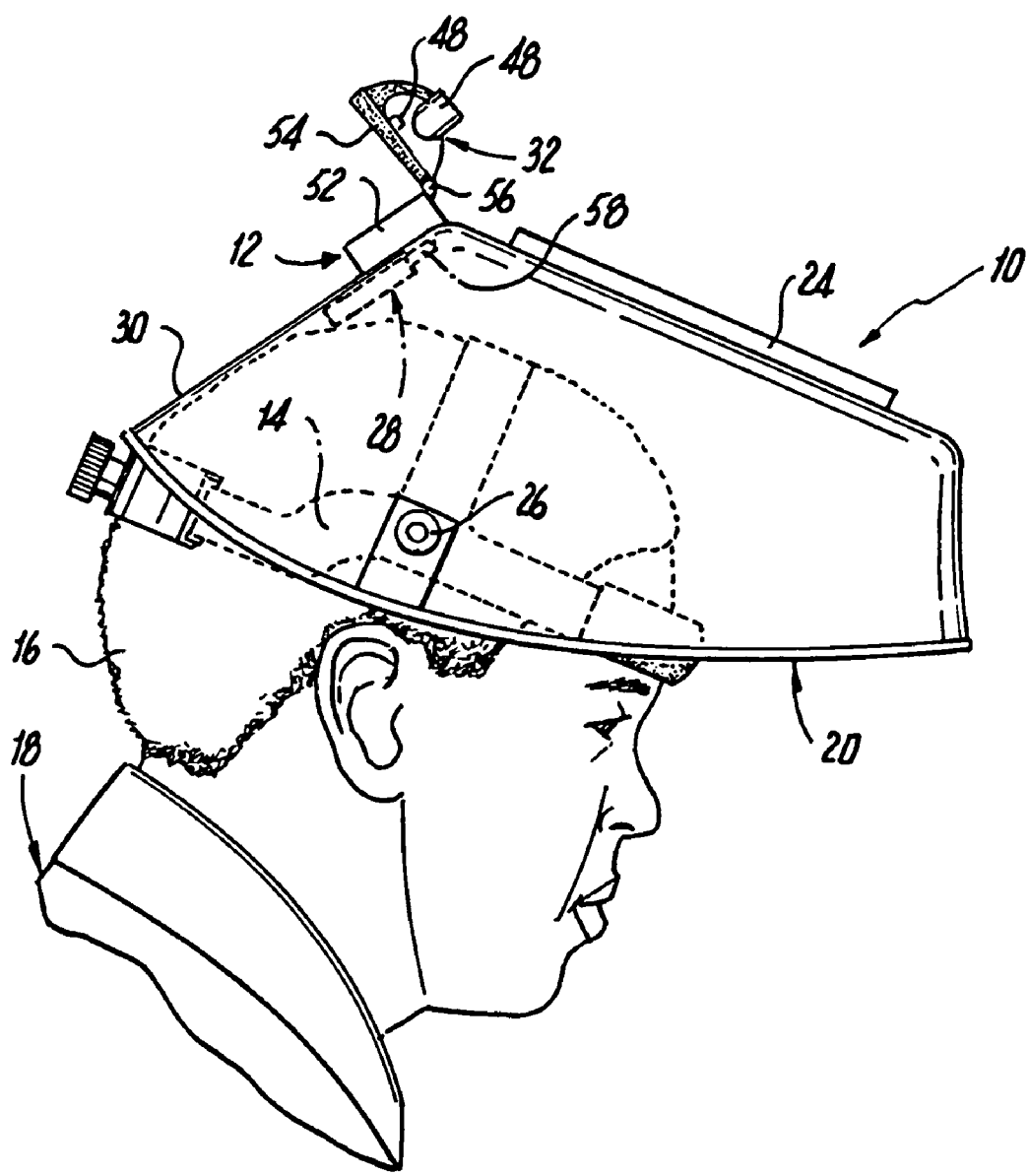
FIG. 6 is a diagrammatic side view taken in the direction of arrow 6 in FIG. 1, showing the face shield of the welding helmet of the present invention raised up in a non-shielding position with the automatic lighting system de-energized.
Figure 7:
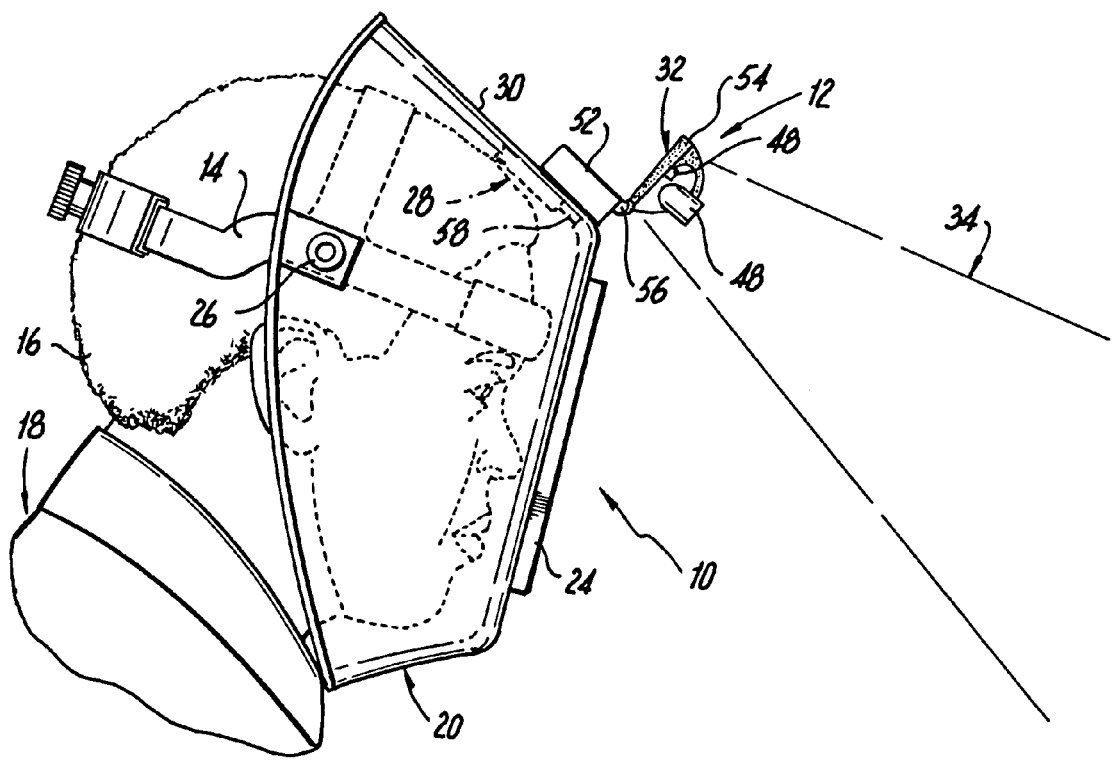
FIG. 7 is a diagrammatic side view similar to FIG. 5, showing the face shield of the welding helmet of the present invention lower down in a shielding position with the automatic lighting system energized.

Referring now to the figures, in which like numerals indicate like parts, and particularly to FIGS. 1 through 7, which are a diagrammatic perspective view of an embodiment of the present invention worn by a welder; an enlarged diagrammatic perspective view of the present invention per se; a further enlarged perspective view, showing in greater detail the automatic lighting system taken in the area enclosed in the dotted circle indicated by arrow 3 in FIG. 2; a still further enlarged diagrammatic perspective view, with parts broken away, taken of the area enclosed in the dotted curve indicated by arrow 4 in FIG. 3, with the cover exploded showing the batteries, gravity sensitive tilt switch and associated components therein; a schematic diagram of the electrical circuit of the automatic lighting system; a diagrammatic side view taken in the direction of arrow 6 in FIG. 1, showing the face shield of the welding helmet of the present invention raised up in a non-shielding position with the automatic lighting system de-energized; and a diagrammatic side view similar to FIG. 5, showing the face shield of the welding helmet of the present invention lower down in a shielding position with the automatic lighting system energized, and as such will be discussed with reference thereto.

The present invention is a welding helmet 10 having an automatic lighting system 12 which comprises the welding helmet 10 having a headband 14 that fits upon a head 16 of a welder 18, and a face shield 20 with a viewing port 22 having a light filtering window 24 that pivots by pivot member 26 on the headband 14 between a raised up non-shielding position and a lower down shielding position. The automatic lighting system 12 has a power source component 28 secured to a bottom surface of a top portion 30 of the face shield 20, and an illumination component 32 secured to a top surface of the top portion 30 of the face shield 20. The power source component 28 is electrically connected to the illumination component 32. When the face shield 20 is pivoted to the raised up non-shielding position the power source component 28 will de-energize the illumination component 32. When the face shield 20 is pivoted to the lower down shielding position the power source component 20 will energize the illumination component 32 to produce a light beam 34 from the illumination component 32, so that the welder 18 can better perceive his/her surroundings and the work area when the face shield is in a lowered position.

The power source component 28 comprises at least one battery 36 and a gravity sensitive tilt switch 38 electrically connected in series loop with the at least one battery 36. An on/off power switch 40 is also electrically connected in the same series loop with the at least one battery 36. A female socket 42 is electrically connected to the power source component 28.

The power source component 28 further comprises a case 44 having a removable cover 46 to retain the at least one battery 36, the gravity sensitive tilt switch 38, the on/off power switch 40 and the female socket 42 therein, wherein the case 44 is optionally removably secured, with mating hook and loop pile fastener material 47 to the bottom surface of the top portion 30 of the face shield 20. The gravity sensitive tilt switch 38 can be a ball type gravity sensitive tilt switch or a mercury type gravity sensitive tilt switch.

The illumination component 32 comprises is illustrated as an array of light emitting diodes 48, but it is to be understood that incandescent lamps, fluorescent lamp, gas filled lamps or other light emitting electrical components might be substituted therefore. The array of light emitting diodes 48 of the illumination component 32 comprises typically two red light emitting diodes, typically two white spot light emitting diodes and typically two white flood light emitting diodes. A multiple position switch 50 controls operation of the two red light emitting diodes, the two white spot light emitting diodes and the two white flood light emitting diodes, so as to permit energizing one set of light emitting diodes at a time and also energizing more then one set of light emitting to simultaneously. Although light are illustrated to show a set of each type of light it is well understood that two is typical for redundancy purposes but any reasonable number could be used from 1 to n without changing the scope of the invention.

The illumination component 32 further comprises a base member 52 secured to the top surface of the top portion 30 of the face shield 20. A headlamp housing 54 is stiffly hinged at 56 to the base member 52 in a manually movable manner by the user so that it will maintain any desired position the user has so adjusted it at. The headlamp housing 54 retains the array of light emitting diodes 48 and the multiple position switch 50. An electrical wire 58 is connected between the array of light emitting diodes 48 and the multiple position switch 50. The electrical wire 58 extends through bottom of the base member 52 and the top portion 30 of the face shield 20. A male plug 60 on a free end of the electrical wire 58 cooperates with and plugs into the female socket 42 in the case 44 of the power source component 28.

It will be understood that each of the elements described above, or two or more together, may also find a useful application in other types of constructions differing from the types described above.

While the invention has been illustrated and described as embodiments of a welding helmet having an automatic lighting system, accordingly it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A welding helmet having an automatic lighting system which comprises:
    a) said welding helmet having a headband that fits upon a head of a welder, and a face shield with a viewing port having a light filtering window that pivots on said headband between a raised up non-shielding position and a lower down shielding position; and
    b) said automatic lighting system having a power source component, secured to a bottom interior surface of a top portion of said face shield, and an illumination component secured to a top exterior surface of said top portion of said face shield, wherein said power source component is electrically connected to said illumination component, wherein when said face shield is pivoted to the raised up non-shielding position said power source component will de-energize said illumination component, and when said face shield is pivoted to the lower down shielding position said power source component will energize said illumination component to produce a light beam from said illumination component, so that the welder can see through said light filtering window of said face shield at an area to be welded or alternatively better perceive his surroundings and a work area, wherein said power source component comprises at least one battery and a gravity sensitive tilt switch electrically connected in a series circuit with said at least one battery, wherein said power source component further comprises an on/off power switch electrically connected in a series circuit with said at least one battery, wherein said power source component further comprises a female socket electrically connected an output of said power source component.

2. The system as recited in claim 1, wherein said power source component further comprises a case having a removable cover to retain said at least one battery, said gravity sensitive tilt switch, said on/off power switch and said female socket therein, wherein said case is secured to said bottom surface of said top portion of said face shield.

3. The system as recited in claim 1, wherein said gravity sensitive tilt switch is a ball type gravity sensitive tilt switch.

4. The system as recited in claim 1, wherein said gravity sensitive tilt switch is a mercury type gravity sensitive tilt switch.

5. The system as recited in claim 1, wherein said illumination component comprises an array of light emitting diodes.

6. The system as recited in claim 5, wherein said array of light emitting diodes of said illumination component comprises two red light emitting diodes, two white spot light emitting diodes and two white flood light emitting diodes.

7. The system as recited in claim 6, wherein said illumination component further comprises a multiple position switch to control operation of said two red light emitting diodes, said two white spot light emitting diodes and said two white flood light emitting diodes.

8. The system as recited in claim 7, wherein said illumination component further comprises;
    a) a base member secured to said top surface of said top portion of said face shield; and
    b) a headlamp housing hinged to said base member in a manual movable manner, wherein said headlamp housing retains said array of light emitting diodes and said multiple position switch.

9. The system as recited in claim 8, further comprising;
    a) an electrical wire connected between said array of light emitting diodes and said multiple position switch, wherein said electrical wire extends through bottom of said base member and said top portion of said face shield; and
    b) a male plug on a free end of said electrical wire which mates with and plugs into said female socket in said case of said power source component.

10. A welding helmet having an automatic lighting system which comprises:
    a) said welding helmet having a self contained illumination component mounted on an exterior surface of said helmet;
    b) said welding helmet having a self contained power source mounted on an interior of said helmet;
    c) means for electrically interconnecting said self contained illumination component with said self contained power source; and
    d) means responsive to the position of said helmet for energizing and de-energizing said illumination component, wherein said means for electrically interconnecting said self contained illumination component with said self contained power source comprises an electrical wire which extends from the interior surface to the exterior surface of said helmet.

11. The system as recited in claim 10, wherein said illumination component further comprises, at least one incandescent lamp.

12. The system as recited in claim 10, wherein said illumination component further comprises, at least one fluorescent lamp.

13. The system as recited in claim 10, wherein said illumination component further comprises, at least one gas filled lamp.

14. The system as recited in claim 10, wherein said self contained power source further comprises, at least one battery.

15. The system as recited in claim 10, wherein said illumination component further comprises, at least one light emitting diode.

16. The system as recited in claim 10, wherein said means for electrically interconnecting said self contained illumination component with said self contained power source further comprises a cooperating male plug and mating female electrical socket.

17. The system as recited in claim 10, wherein said means for electrically interconnecting said self contained illumination component with said self contained power source further comprises an on/off power switch electrically connected in a series loop with said at least one battery of said self contained power source.

18. The system as recited in claim 10, wherein said means for electrically interconnecting said self contained illumination component with said self contained power source further comprises an on/off power switch electrically connected in a series loop with said at least one battery of said self contained power source.

19. The system as recited in claim 10, wherein said means for electrically interconnecting said self contained illumination component with said self contained power source further comprises a multiple position switch electrically connected in a series loop with said at least one self contained illumination component and said self contained power source.

20. The system as recited in claim 10, wherein said means for electrically interconnecting said self contained illumination component with said self contained power source further comprises a gravity sensitive tilt switch electrically connected in a series loop with said at least one self contained illumination component and said self contained power source.

21. The system as recited in claim 20, wherein said gravity sensitive tilt switch is a ball type gravity sensitive tilt switch.

22. The system as recited in claim 20, wherein said gravity sensitive tilt switch is a mercury type gravity sensitive tilt switch.

\* \* \* \* \*